(12) United States Patent
Andersohn

(10) Patent No.: US 8,439,903 B2
(45) Date of Patent: May 14, 2013

(54) SYSTEMS AND METHODS FOR DELIVERING LIGHT TO A SURGICAL SITE

(75) Inventor: Lutz Andersohn, Glencoe, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 232 days.

(21) Appl. No.: 12/897,035

(22) Filed: Oct. 4, 2010

(65) Prior Publication Data

US 2012/0083665 A1 Apr. 5, 2012

(51) Int. Cl.
*A61B 18/18* (2006.01)
(52) U.S. Cl.
USPC .......... 606/10; 606/4; 606/12; 128/898
(58) Field of Classification Search .......... 606/4–6, 606/10–13; 607/88, 89; 128/898
See application file for complete search history.

(56) References Cited

U.S. PATENT DOCUMENTS

| 4,580,557 | A  | * | 4/1986  | Hertzmann     | 606/12 |
|-----------|----|---|---------|---------------|--------|
| 6,458,120 | B1 | * | 10/2002 | Shen et al.   | 606/10 |
| 2004/0078030 | A1 | * | 4/2004  | Lin        | 606/5  |
| 2008/0004608 | A1 | * | 1/2008  | Dacquay et al. | 606/4 |
| 2010/0049180 | A1 | * | 2/2010  | Wells et al.  | 606/12 |

* cited by examiner

*Primary Examiner* — Ahmed Farah
(74) *Attorney, Agent, or Firm* — Jeffrey B. Powers

(57) ABSTRACT

An ophthalmic surgery system for delivering light to a surgical site includes an ophthalmic surgical console including a light source to generate light and a processor operably coupled to the light source and a surgical handpiece operably coupled to the ophthalmic surgical console via an optical fiber for delivering light from the from the light source to a surgical site. The processor is configured to adjust the light source to ensure an output light level at the surgical site is substantially consistent over a period of time.

11 Claims, 2 Drawing Sheets

SYSTEMS AND METHODS FOR DELIVERING LIGHT TO A SURGICAL SITE

BACKGROUND

1. Field

The present disclosure is generally directed to systems and methods for delivering light to a surgical site.

2. Description of the Related Art

The statements in this section merely provide background information related to the present disclosure and may not constitute prior art.

In eye surgery, a number of different ophthalmic procedures are known to include disposing a surgical handpiece proximate to a patient's eye, and often inserted into the patient's eye, to provide illumination. The surgical handpiece is connected to a light source enclosed by a surgical system, generally via an optical fiber for transmitting light from the surgical system to the patient's eye.

There exists a need for improved systems and methods for delivering light to a surgical site.

BRIEF DESCRIPTION OF THE DRAWINGS

The drawings described herein are for illustration purposes only and are not intended to limit the scope of the present disclosure in any way.

DETAILED DESCRIPTION OF THE PREFERRED EMBODIMENT

The following description is merely exemplary in nature and is not intended to limit the present disclosure, application, or uses.

Figure 1:
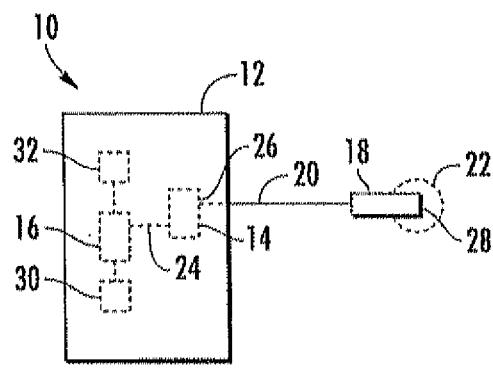
FIG. 1 is block diagram of an ophthalmic surgery system according to one example embodiment of the present disclosure.

According to one embodiment of the present disclosure, an ophthalmic surgery system 10 is illustrated in FIG. 1. The ophthalmic surgery system 10 includes an ophthalmic surgical console 12 having a light source 14 and a processor 16 operably coupled to the light source 14. The ophthalmic surgery system 10 includes a surgical handpiece 18 operably coupled to the ophthalmic surgical console 12 via an optical fiber 20 for delivering a light from the light source 14 to a surgical site 22. In use, the processor 16 provides a command light level 24 to the light source 14, which generates an actual light level 26 transmitted through the optical fiber 20, resulting in an output light level 28 at the surgical site 22.

As recognized by the inventor of the present disclosure, when the ophthalmic surgery system 10 operates over a period of time, one or more properties of the ophthalmic surgery system 10 may vary, causing the output light level 28 to the surgical site 22 to vary. Accordingly, the processor 16 is configured to adjust the light source 14 to ensure the output light level 28 at the surgical site 22 is substantially consistent over a period of time. In this manner, the output light level 28 is substantially consistent, without awareness of, interaction and/or alteration by a user, e.g., a surgeon, a surgical technician, etc.

The processor 16 is configured to adjust the light source 14, based on a property of the optical fiber 20 and a property of the light source 14. It should be appreciated that in other embodiments, a processor may be configured to adjust the light source based on one or more properties of an optical fiber and/or one or more properties of a light source.

Figure 2:
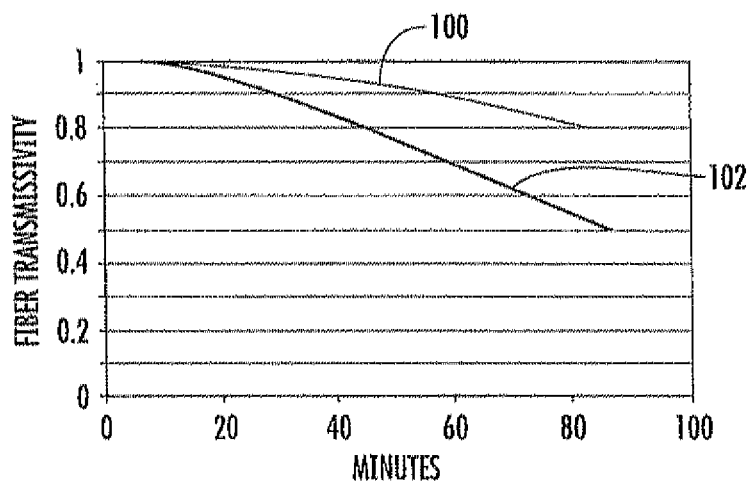
FIG. 2 is diagram illustrating transmissivity of an optical fiber included in the ophthalmic surgery system of FIG. 1, over several minutes.

In the embodiment of FIG. 1, the property of the optical fiber 20 includes transmissivity of the optical fiber 20. When light is supplied through an optical fiber over a period of time, transmissivity of the optical fiber degrades. FIG. 2 illustrates two transmissivities of the optical fiber 20 over about one hundred minutes—transmissivity 100 for a high light level and transmissivity 102 for a medium light level. As shown, degradation of transmissivity of the optical fiber 20 depends on an amount of light transmitted through the optical fiber 20. Accordingly, the transmissivity 100 degrades more rapidly than the transmissivity 102, due to the high light level versus the medium light level through the optical fiber 20.

The processor 16 of the ophthalmic surgical console 12 is configured to adjust the light source 14 to compensate for the degradation of transmissivity of the optical fiber 20 to ensure the output light level 28 at the surgical site 22 is substantially consistent.

Specifically, the processor 16 determines a total quantity of light supplied to the optical fiber 20, which is an integral of the light level over an amount of time the light level is supplied to the optical fiber 20. In the embodiment of FIG. 1, the total quantity of light is calculated by summing the command light level 24 periodically, e.g., per second. After determining the total quantity of light, the processor 16 selects a fiber transmissivity stored in memory 30 operably coupled to the processor 16, based on the total quantity of light. The memory 30 may be RAM, ROM, e.g., an EEPROM (incorporated with or apart from the processor 16), or other known memories. The memory 30 includes a plurality of optical fiber transmissivities, which have been calculated, based on at least one characteristic of the optical fiber 20, or measured from the optical fiber 20 or an optical fiber having a similar shape and/or size to the optical fiber 20. The memory 30 stores at least the information shown in the diagram of FIG. 2.

Based on the optical fiber transmissivity, the processor 16 calculates a command light level 24 ("CLL") to be generated by the light source 14 necessary for the output light level 28 to be substantially consistent over a period of time, using the following equation:

$$CLL = \text{User Set} / \text{Fiber Transmissivity Factor}$$

The user set is a user setting received by the ophthalmic surgical console 12, via an input device 32 operably coupled to the processor 16, to indicate a user preferred light level. The input device 32 may include a touchscreen display, a button, a switch, a keyboard, or other suitable input device, etc. In at least one embodiment, a user setting may be altered by a user during one or more surgical procedures.

Figure 3:
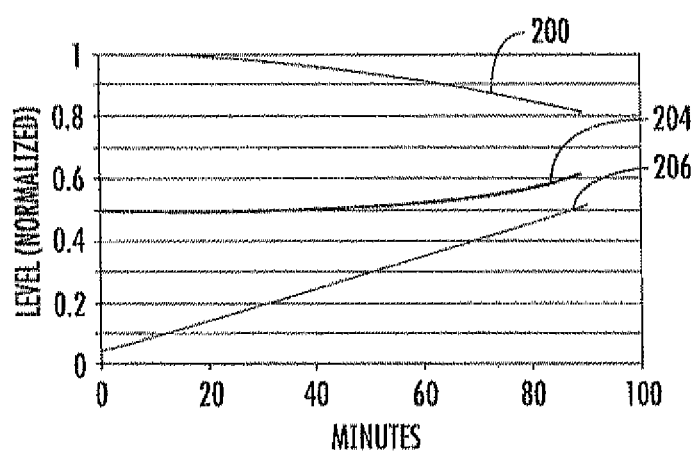
FIG. 3 is a diagram illustrating a command light level, relative to transmissivity of an optical fiber of FIG. 1.

In one example calculation, after a period of time of 60 minutes, a fiber transmissivity factor for the optical fiber 20 (for a medium light level) is about 0.9, as shown in FIG. 2, by dashed line. The top line of FIG. 2 may represent the fiber transmissivity factor for a low light level and the bottom line a fiber transmissivity factor for a high light level. For a user setting of 70% or 0.7, after 60 minutes, the command light level 24 provided to the light source 14 is about 77.7% to maintain a substantially consistent 70% output light level, as requested by the user at the outset of the 60 minutes period of time. Subsequently, the processor 16 adjusts the light source 14 to provide an actual light level of about 77.7%. FIG. 3 illustrates one example adjustment of the light source 14 over about 90 minutes. As the transmissivity 200 of the optical fiber 20 degrades, the command light level 204 is increased to ensure the output light level at the surgical site 22 is substantially consistent over said period of time. The total quantity of light 206 supplied through the optical fiber 20 is also shown.

In the embodiment of FIG. 1, the processor 16 is configured to periodically calculate the command light level 24 to ensure that minimal adjusts—unnoticeable by a user—are made to provide a substantially consistent output light level 28 to the surgical site 22. In the above example, a previous adjustment may have set the light source at 77.6%, providing only a 0.1% adjustment to provide the substantially consistent output light level 28 to the surgical site 22. In at least one embodiment, a processor may only make adjustments above a minimum threshold. For example, a processor may be configured to adjust a light source, only when an adjustment is at least equal to 0.3%. For the adjustment of 0.1% (77.7%-77.6%) per the example described above, the processor does not adjust the light source. Instead, the processor permits the necessary adjustment to reach 0.3% or more before adjusting the light source. In this manner, the substantially consistent output light level may be ±0.3%. It should be appreciated that in various embodiment of the present disclosure, substantially consistent may include ±0.5%, ±1.0%, ±2.0%, or ±5.0%, etc. In some embodiments, substantially consistent may be a different deviation considered unnoticed by a user.

The processor 16 may employ various periods of time between calculations and/or adjustments to minimize a magnitude of an adjustment and/or a user's awareness of an adjustment. For example, a processor may be configured to calculate a command light level and/or adjust the command light level to a light source every one second, 5 seconds, 10 seconds, 30 seconds, 1 minute, 3 minutes, 10 minutes, 15 minutes, or other suitable times, etc. An output light level may also be held substantially consistent over different periods of time. For example, a period of time may be the duration of an ophthalmic surgical procedure, the duration of multiple ophthalmic surgical procedures, the life of a light source, or another suitable period of time, etc.

Figure 4:
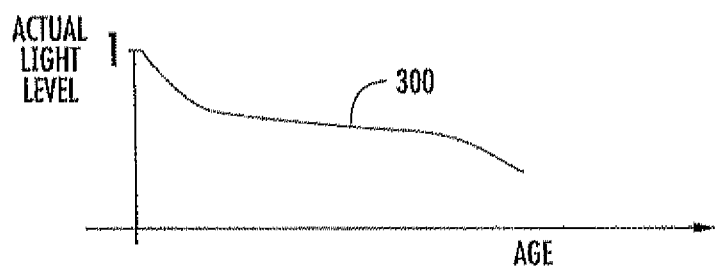
FIG. 4 is a diagram illustrating an actual light level from a light source included in the ophthalmic surgery system of FIG. 1, over a life of the light source.

Referring again to FIG. 1, the processor 16 is also configured to adjust the light source 14 based on a property of the light source 14. The property of the light source includes the brightness of the light source 14, based on at least one of manufacturing difference brightness and lifetime degradation of the brightness. The light source 14 may be an LED, a laser, an incandescent lamp, a xenon lamp, etc. Over a period of time, such as a life of the light source, brightness of the light source 14 may be degraded. For example, as shown in FIG. 4, a light source generally degrades over a period of time, for example typical lamp life for ophthalmic surgery is in a range of about 400-800 hours. The degradation of the brightness is the difference between the command light level (100% for FIG. 4) and the actual light level 300.

The processor 16 of the ophthalmic surgical console 12 is configured to adjust the light source 14 to compensate for a degradation of brightness of the light source 14 to ensure a substantially consistent output light level 28 at the surgical site 22. The processor 16 calculates the command light level 24 from the light source 14, based on an age factor of the light source 14 (and the fiber transmissivity factor described above), as follows:

$$CLL = \text{User Set}/(\text{Age Factor} \times \text{Fiber Transmissivity Factor})$$

Figure 5:
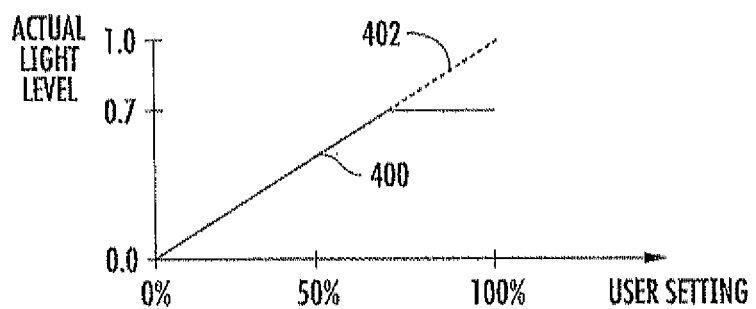
FIG. 5 is a diagram illustrating an actual light level, relative to a user setting, from a light source at the end of its life.

As the age factor decreases as shown in FIG. 4, the processor 16 adjusts the light source 14 to compensate for the degradation of the brightness of the light source 14. In this manner, the output light level at the surgical site 22 is substantially consistent over a period of time. Additionally, after a period of time, an age factor of a light source may eventually limit an actual light level (notwithstanding a higher command light level). In the example of FIG. 5, the actual light level 400 is limited to 0.7 or 70% by the age factor, regardless of a user setting 402 in excess of 70%. It should be appreciated that an age of a light source may be a time from manufacture of the light source or a time the light source has been operational. In at least one example embodiment, a processor may adjust a light source, solely based on a user setting and an age factor.

The age factors shown in the diagram of FIG. 4 is stored in memory 30 associated with the processor 16. The age factors stored in memory 30 may be measured from at least one similar light source over its lifetime or a different suitable duration.

Alternatively or additionally, a property of a light source may include an attenuation factor, which substantially normalizes brightness differences between different light sources during production of ophthalmic surgical consoles. The attenuation factor equals a minimum light source brightness of a number of light sources divided by an actual light level of said light source, when tested during manufacturing. In one example, for a command light level of 1.0, a first light source may have an actual light level of 0.95 and a second light source may have an actual light level of 0.92. An attenuation factor for the first light source is 0.96 (0.92/0.95), and an attenuation factor for the second light source is 1.0 (0.92/0.92). The attenuation factor of the first light course normalized the actual light level of the first light source so that the actual light levels of the first and second light sources are substantially the same. The attenuation factor is stored in memory 30, and recalled by the processor 16 as needed. An attenuation factor may be employed to calculate a command light level, using the following equation:

$$CLL = \text{User Set} \times \text{Attenuation Factor}$$

It should be appreciated that an attenuation factor may be omitted in some embodiments of the present disclosure. In other embodiments, an attenuation factor may be employed to provide a reserved light level (not accessible to a user setting), usable to compensate for degradation of transmissivity of an optical fiber, degradation of a light source, or other factors or changes in an ophthalmic surgery system to ensure an output light level at a surgical site is substantially consistent over a period of time.

In various embodiments of the present disclosure, a command light level may be calculated as a function of an age factor and an attenuation factor, using the following equation:

$$CLL = (\text{User Set} \times \text{Attenuation Factor})/\text{Age Factor}$$

It should be appreciated that one or both of an attenuation factor and an age factor may be omitted as a basis for adjusting a light source in other embodiments. In yet another embodiment, a processor may adjust a light source as a function of a fiber transmissivity factor, an attenuation factor, and an age factor, using the following equation:

$$CLL = (\text{User Set} \times \text{Attenuation Factor})/(\text{Age Factor} \times \text{Fiber Transmissivity Factor})$$

It should be appreciated that a different permutation of factors associated with properties of an ophthalmic surgery system, as disclosed herein and one or more others, may be employed, alone or in combination, to adjust a light source to ensure an output light level at the surgical site is substantially consistent over a period of time.

It should be appreciated that after the period of time, an ophthalmic surgery system may not be able to provide a substantially consistent output light level. At that point, a processor may provide a command light level to a light source for a maximum light level, i.e., 1.0 or 100%. In various embodiments of the present disclosure, a light source may be replaced when a substantially consistent output light level cannot be maintained.

According to one embodiment of the present disclosure, an ophthalmic surgery system includes an ophthalmic surgical console including a light source to generate light, a processor, and a memory operably coupled to the processor. The ophthalmic surgery system also includes a surgical handpiece operably coupled to the ophthalmic surgical console via an optical fiber for delivering light from the light source to a surgical site and a program stored in the memory and executable by the processor for adjusting the light source to ensure an output light level at the surgical site is substantially consistent over a period of time.

Although several aspects of the present disclosure have been described above with reference to delivering light to a surgical site, it should be understood that various aspects of the present disclosure are not limited to delivering light to a surgical site, and can be implemented in a variety of other ophthalmic applications.

By implementing any or all of the teachings described above, a number of benefits and advantages can be attained including improved reliability, reduced down time, elimination or reduction of redundant components or systems, avoiding unnecessary or premature replacement of components or systems, and a reduction in overall system and operating costs.

I claim:

1. An ophthalmic surgery system for delivering light to a surgical site, the ophthalmic surgery system comprising:
   an ophthalmic surgical console including a light source for generating light and a processor operably coupled to the light source; and
   a surgical handpiece operably coupled to the ophthalmic surgical console via an optical fiber for delivering light from the light source to a surgical site, the processor being configured to adjust the light source based on at least a change in transmissivity of the optical fiber to ensure an output light level at the surgical site is substantially consistent over a duration of an ophthalmic surgical procedure.

2. The ophthalmic surgery system of claim 1, wherein the processor is configured to adjust the light source, based on at least one property of the light source.

3. The ophthalmic surgery system of claim 2, wherein the at least one property includes an age of the light source.

4. The ophthalmic surgery system of claim 1, further comprising a memory operably coupled to the processor, the memory including a plurality of fiber transmissivity factors, the processor configured to adjust the light source as a function of at least one of the plurality of transmissivity factors.

5. An ophthalmic surgery system comprising an ophthalmic surgical console including a light source to generate light, a processor, and a memory operably coupled to the processor, a surgical handpiece operably coupled to the ophthalmic surgical console via an optical fiber for delivering light from the light source to a surgical site, and a program stored in the memory and executable by the processor for adjusting the light source based on at least a change in transmissivity of the optical fiber stored in the memory to ensure an output light level at the surgical site is substantially consistent over a duration of an ophthalmic surgical procedure.

6. A method of delivering light from a light source of an ophthalmic surgical console to a surgical site via an optical fiber, the method comprising:
   identifying an output light level at the surgical site;
   providing a processor configured to calculate a command light level based on at least a change in transmissivity of the optical fiber; and
   adjusting the light source according to the command light level to ensure the output light level is substantially consistent over a duration of an ophthalmic surgical procedure.

7. The method of claim 6, wherein adjusting the light source includes calculating a command light level, based on at least one property of the light source, and adjusting the light source according to the command light level.

8. The method of claim 7, wherein the at least one property of the light source is an age of the light source.

9. The method of claim 6, wherein adjusting the light source includes calculating a command light level, as a function of at least one of a fiber transmissivity factor, an age factor, and an attenuation factor, and adjusting the light source according to the command light level.

10. The method of claim 9, wherein calculating a command light level includes periodically calculating a command light level.

11. The method of claim 6, wherein adjusting the light source includes periodically adjusting the light source.

* * * * *